(12) United States Patent
Oka et al.

(10) Patent No.: US 8,949,043 B2
(45) Date of Patent: Feb. 3, 2015

(54) SURFACE INSPECTING APPARATUS AND METHOD FOR CALIBRATING SAME

(75) Inventors: Kenji Oka, Hitachinaka (JP); Kenji Mitomo, Hitachinaka (JP); Kenichiro Komeda, Kumamoto (JP)

(73) Assignee: Hitachi High-Technologies Corporation, Tokyo (JP)

( * ) Notice: Subject to any disclaimer, the term of this patent is extended or adjusted under 35 U.S.C. 154(b) by 753 days.

(21) Appl. No.: 13/202,734

(22) PCT Filed: Feb. 2, 2010

(86) PCT No.: PCT/JP2010/051441
§ 371 (c)(1),
(2), (4) Date: Nov. 2, 2011

(87) PCT Pub. No.: WO2010/098179
PCT Pub. Date: Sep. 2, 2010

(65) Prior Publication Data
US 2012/0046884 A1     Feb. 23, 2012

(30) Foreign Application Priority Data
Feb. 27, 2009  (JP) .................... 2009-046279

(51) Int. Cl.
*G01N 21/94*     (2006.01)
*G01N 21/93*     (2006.01)
*G01N 21/95*     (2006.01)

(52) U.S. Cl.
CPC ............ *G01N 21/9501* (2013.01); *G01N 21/93* (2013.01); *G01N 2201/103* (2013.01)
USPC ............................ 702/40; 356/73; 356/237.1

(58) Field of Classification Search
CPC ................. G01N 21/9501; G01N 21/95684; G01N 21/93; G01N 2201/103; H01L 22/12; H01L 21/67288; G01R 31/311; G06T 2207/30148; G06T 7/0004
USPC .................. 702/28, 35, 40, 104, 134; 356/73, 356/237.1, 237.2, 237.3, 237.5; 438/18
See application file for complete search history.

(56) References Cited

U.S. PATENT DOCUMENTS 6,774,987 B2 *  8/2004  Komatsu et al. ................ 356/73
7,719,669 B2 *  5/2010  Matsui et al. ............. 356/237.1

OTHER PUBLICATIONS

Japanese Office Action, and English translation thereof, issued in Japanese Patent Application No. 2009-046279 dated Jul. 10, 2012.

* cited by examiner

*Primary Examiner* — John H Le
(74) *Attorney, Agent, or Firm* — McDermott Will & Emery LLP

(57) ABSTRACT

While an illumination optical system is irradiating the surface of a contaminated standard wafer with illumination light, this illumination light is scanned over the surface of the contaminated standard wafer, then detectors of a detection optical system each detect the light scattered from the surface of the contaminated standard wafer, next a predefined reference value in addition to detection results on the scattered light is used to calculate a compensation parameter "Comp" for detection sensitivity correction of photomultiplier tubes of the detectors, and the compensation parameter "Comp" is separated into a time-varying deterioration parameter "P", an optical characteristics parameter "Opt", and a sensor characteristics parameter "Lr", and correspondingly managed. This makes is easy to calibrate the detection sensitivity.

11 Claims, 6 Drawing Sheets

Fig. 5

COMPENSATON PARAMETER ARITHMETIC RESULT CONFIRMATION

| No. | Recipe | Last update | Comment |
|-----|--------|-------------|---------|
| 1 | Cal-Recipe1 | 2008/03/06 17:10:15 | PERIODIC CALIBRATION |
| 2 | Cal-Recipe2 | 2008/03/06 17:12:15 | PERIODIC CALIBRATION |
| 3 | Cal-Recipe3 | 2008/03/06 17:14:15 | PERIODIC CALIBRATION |
| 4 | Cal-Recipe4 | 2008/03/06 17:16:15 | PERIODIC CALIBRATION |
| 5 | Cal-Recipe5 | 2008/03/06 17:18:15 | PERIODIC CALIBRATION |
| 6 | | | |
| 7 | | | |
| 8 | | | |
| 9 | | | |
| 10 | | | |

SUMMARY
HISTORY
UPDATE
CANCEL

Recipe: Cal-Recipe1   Last Update: 2008/03/06 17:10:15

| SIZE [nm] | DETECTOR | REFERENCE VALUES | | DETECTION VALUES | | UPDATE VALUE | PREVIOUS VALUES | | |
|---|---|---|---|---|---|---|---|---|---|
| | | VOLTAGE VALUE | MARGIN | VOLTAGE VALUE | DIFFER- ENCE | | OPTICAL SYSTEM | DETERIO- RATION | SENSOR CHARAC- TERISTICS |
| 50 | L1 | 2200 | 25 | 2181 | -19 | 1.004 | 1.020 | 1.000 | 0.985 |
| | L2 | 2200 | 25 | 2192 | -8 | 1.002 | 1.050 | 1.000 | 0.980 |
| | L3 | 2200 | 25 | 2181 | -19 | 1.004 | 1.060 | 1.000 | 0.975 |
| | L4 | 2200 | 25 | 2150 | -50 | 1.011 | 1.080 | 1.000 | 0.988 |
| | L5 | 2200 | 25 | 2202 | 2 | 1.000 | 1.090 | 1.000 | 0.975 |
| | L6 | 2200 | 25 | 2211 | 11 | 0.998 | 1.020 | 1.000 | 0.980 |
| 60 | H1 | 2320 | 25 | 2315 | -5 | 1.001 | 1.045 | 1.000 | 0.990 |
| | H2 | 2400 | 25 | 2403 | 3 | 0.999 | 1.030 | 1.000 | 0.990 |
| | H3 | 2560 | 25 | 2560 | 0 | 1.000 | 1.020 | 1.000 | 0.980 |
| | H4 | 2400 | 25 | 2400 | 0 | 1.000 | 1.010 | 1.000 | 0.985 |

Fig. 6

SUMMARY CONFIRMATION SCREEN

| CONDISION SET NUMBER | | 1 | 2 | 3 | 4 | 5 |
|---|---|---|---|---|---|---|
| ILLUMINATION ANGLE | | OBLIQUE | OBLIQUE | OBLIQUE | OBLIQUE | PERPEN-DICULAR |
| POLARIZING CONDITIONS | | P-N | S-N | C-N | S-P | P-N |
| LIGHT DETECTORS | L1 | -19 | -6 | -19 | -6 | -100 |
| | L2 | -8 | 2 | -8 | 2 | -90 |
| | L3 | -19 | -8 | 19 | -8 | -60 |
| | L4 | -50 | -60 | -70 | -65 | -80 |
| | H1 | 2 | 22 | 2 | 22 | -69 |
| | H2 | 11 | 7 | 11 | 12 | -80 |
| | H3 | -5 | -12 | -14 | 7 | -78 |
| | H4 | 3 | 14 | 3 | 11 | -80 |

RETURN

SURFACE INSPECTING APPARATUS AND METHOD FOR CALIBRATING SAME

RELATED APPLICATIONS

This application is the U.S. National Phase under 35 U.S.C. §371 of International Application No. PCT/JP2010/051441, filed on Feb. 2, 2010, which in turn claims the benefit of Japanese Application No. 2009-046279, filed on Feb. 27, 2009, the disclosures of which Applications are incorporated by reference herein

TECHNICAL FIELD

The present invention relates to an inspecting apparatus for detecting a foreign substance, flaw, defect, dirt, etc. (hereinafter collectively referred to as a foreign object) present on the surfaces of semiconductor wafers and other materials to be inspected. The invention is also directed to a method for calibrating the apparatus.

BACKGROUND ART

To suppress deterioration in quality and yield in semiconductor device manufacturing processes, it is important to quantitatively understand the cleanliness levels of various manufacturing apparatuses and process sites, and to appropriately control the manufacturing processes. To this end, there is a need to detect a foreign substance, flaw, defect, dirt, etc. (hereinafter collectively referred to as a foreign object) present on the surfaces of the semiconductor wafers (hereinafter, referred to simply as wafers) and statistically control the kind, size, quantity, etc. of a foreign object detected. Accordingly, wafer surface inspection with surface inspecting apparatuses has traditionally taken place in the semiconductor device manufacturing processes.

A known type of surface inspecting apparatus for detecting a foreign object on the surface of a wafer achieves the detection by irradiating the wafer surface with such inspection light as laser light, and detecting the light reflected or scattered from the wafer surface (See Patent Document 1, for example).

PRIOR ART REFERENCES

Patent Document

Patent Document 1: JP-9-304289-A

SUMMARY OF THE INVENTION

Problem to be Solved by the Invention

Controlling the manufacturing processes appropriately by the statistical control mentioned above presupposes ensuring the accuracy of the information used for the statistical control. To meet this requirement, it is absolutely necessary to calibrate the surface inspecting apparatus periodically and maintain its constant detecting accuracy during surface inspection.

Detection sensitivity of a surface inspecting apparatus is calibrated by, for example, irradiating a wafer surface provided with a foreign object sample of a standard particle size (hereinafter, this wafer is referred to as the contaminated standard wafer) with illumination light, then detecting the light scattered from the foreign object sample, and adjusting the detection sensitivity so that a relationship between the particle size of the foreign object sample and a detection value of the scattered light matches a predetermined calibration curve.

During such calibration of the detection sensitivity, it is necessary for an operator to verify the adequacy of the detection sensitivity adjustment while synthetically considering various parameters such as the deterioration states and temperature drifts of the elements constituting the surface inspecting apparatus. The calibration of the detection sensitivity has therefore been very complex.

The present invention has been made with the above in mind, and an object of the invention is to provide a surface inspecting apparatus easily correctible in detection sensitivity, and a method for calibrating the apparatus.

Means for Solving the Problem

In order to attain the above object, an aspect of the present invention includes: means that irradiates with illumination light the surface of a body to be inspected; means that scans the light irradiated from the irradiating means over the surface of the to-be-inspected body; a plurality of means that each detect the light scattered from the surface of the body to be inspected; means that generates measuring light which serves as a reference for measuring detection sensitivity of each of the plurality of light detection means; means that uses a predefined reference value, as well as detection results on the measuring light incident upon the light detection means from the measuring light generating means, to compute a sensitivity correction value for correcting the detection sensitivity of each light detection means; and separation arithmetic means that separates the sensitivity correction value into element parameters corresponding to a plurality of factors influential upon detection sensitivity of the surface inspecting apparatus.

Effects of the Invention

The calibration of detection sensitivity in a surface inspecting apparatus is facilitated in the present invention.

BRIEF DESCRIPTION OF THE DRAWINGS

FIG. 5 shows a screen for confirming compensation parameter arithmetic results in the calibration process for the surface inspecting apparatus according to the embodiment of the present invention;

FIG. 6 shows a screen for confirming a summary in the calibration process for the surface inspecting apparatus according to the embodiment of the present invention.

MODE FOR CARRYING OUT THE INVENTION

Hereunder, an embodiment of the present invention will be described referring to the accompanying drawings.

(1) Surface Inspecting Apparatus Configuration

Figure 1:
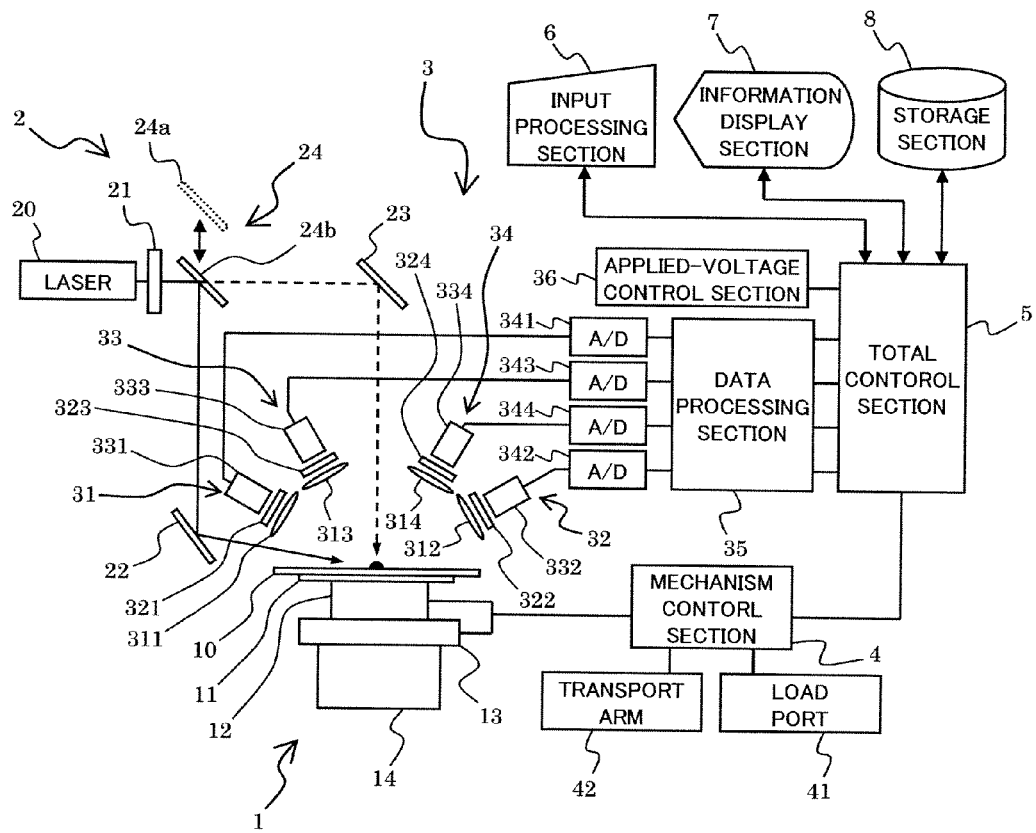
FIG. 1 is a schematic diagram showing an overall configuration of a surface inspecting apparatus according to an embodiment of the present invention.

FIG. 1 is a diagram showing an overall configuration of a surface inspecting apparatus according to the embodiment.

Referring to FIG. 1, the surface inspecting apparatus according to the embodiment includes: a wafer mounting unit 1 on which is mounted a wafer 10 that is an example of a body to be inspected (e.g., the wafer, a hard disk, a liquid-crystal substrate, or the like); an illumination optical system 2 that irradiates the surface of the wafer 10 (i.e., the surface to be inspected) with illumination light; a detection optical system 3 that detects the light scattered from the surface of the wafer 10; a mechanism control unit 4 that controls a driving system in the surface inspecting apparatus; and a total control unit 5 that controls the surface inspecting apparatus in its entirety.

The wafer mounting unit 1 includes a wafer chuck 11 that uses suction to hold the wafer 10, a rotary stage 12 that holds the wafer chuck 11, a rectilinear stage 13 that holds the rotary stage 12, and a base 14 that holds the rectilinear stage 13.

The rotary stage 12 is rotationally driven with respect to the rectilinear stage 13 and rotationally drives the wafer chuck 11 together with the wafer 10. The rectilinear stage 13 is rectilinearly driven with respect to the base 14 and rectilinearly drives the rotary stage 12. While the surface of the wafer 10 (i.e., the surface to be inspected) is being irradiated with the illumination light, the wafer 10 is rotationally driven or rectilinearly driven or driven in both rotational and rectilinear forms, so that the illumination light is scanned over the surface of the wafer 10.

The illumination optical system 2 includes: a laser light source 20 that generates and emits, for example, the argon (Ar) laser light, nitrogen laser light, helium-cadmium (He-Cd) laser light, excimer laser light, or other laser light that is the illumination light; an illumination light polarizing filter 21 that transforms the laser light emitted from the laser light source 20 into polarized light; reflecting mirrors 22 and 23 that each reflect the laser light passed through the illumination light polarizing filter 21; and an illumination angle switching mirror 24 that is driven by a driving unit not shown, and switches a traveling route (optical path) of the laser light.

If the illumination angle switching mirror 24 is disposed on the optical path of the illumination light by the driving unit (not shown), that is, at a position 24a in FIG. 1, the illumination light that has been emitted from the laser light source 2 is directed obliquely (at an angle of, for example, 30° or less) to the surface of the wafer 10 via the illumination angle switching mirror 24 and the reflecting mirror 22. If the illumination angle switching mirror 24 is shifted away from the optical path of the illumination light, that is, positioned at a position 24b in FIG. 1, the emitted illumination light from the laser light source 2 is directed at a substantially vertical angle to the surface of the wafer 10 via the reflecting mirror 23. The position of the illumination angle switching mirror 24 is controlled by the total control unit 5.

If a foreign object is present at an irradiation position of the illumination light on the wafer 10, this causes scattered light according to a particular size and shape of the foreign object.

The detection optical system 3 includes: a plurality of detectors, 31 to 34, that each detect the light scattered from the surface of the wafer 10; A/D converters 341 to 344 that each convert analog detection signals output from one of the detectors 31 to 34, into digital detection signal form; a data processing unit 35 that conducts data processing (to be described later herein) upon the detection signals from the A/D converters 341 to 344 and inputs the processed data to the total control unit 5; and an applied-voltage control unit 36 that controls a voltage applied to each of photomultiplier tubes 331 to 334 (also to be described later) of the detectors 31 to 34 in accordance with a command from the total control unit 5 (the voltage is hereinafter referred to as the applied voltage).

The detectors 31, 32 are arranged so that an angle of elevation with the surface of the wafer 10 as a reference is equal to or less than a predetermined reference angle of say, 30°. Hereinafter, such detectors 31, 32 are referred to specially as the low-angle detection optical system. The detectors 33, 34 are arranged to form an angle of elevation greater than the reference angle. Hereinafter, such detectors 33, 34 are referred to specially as the high-angle detection optical system.

The low-angle detection optical system and the high-angle detection optical system have the respective detectors arranged around the irradiation position of the illumination light on the wafer 10. In order to avoid complicatedness of the drawing, FIG. 1 shows two detectors, 31 and 32, on behalf of the low-angle detection optical system, and two other detectors, 33 and 34, on behalf of the high-angle detection optical system, respectively; illustration and description of all other detectors being omitted.

The detector 31 includes a condensing lens 311 for condensing the light scattered from the wafer 10, a detected-light polarizing filter 321 for converting the scattered light that the condensing lens 311 has condensed, into polarized light, and a photomultiplier tube (PMT) 331 for receiving the scattered light that has been passed through the detected-light polarizing filter 321, then converting the amount of received light into an equivalent amount of electric current, and sending a consequential detection signal as an input signal to the A/D converter 341. In addition, the detectors 32 to 34 have substantially the same configuration as that of the detector 31, and each of the three detectors includes one of condensing lenses 312 to 314, one of detected-light polarizing filters 322 to 324, and one of photomultiplier tubes 332 to 334.

Each A/D converter 341 to 344 upon receiving an analog detection signal (current signal) output from the appropriate detector 31 to 34, converts the analog detection signal into a digital detection signal (voltage signal) and then sends the digital signal as an input signal to the data processing unit 35.

The data processing unit 35 conducts data processing to extract, from the detection signals received from the A/D converters 341 to 344, only a detection signal whose voltage value (hereinafter, referred to as the detection voltage value) has exceeded a predefined threshold level, and then sends the extracted detection signal as an input signal to the total control unit 5. The threshold level used for data processing in the data processing unit 35 is set up independently for each detection signal from the detectors 31 to 34, and the independent threshold levels are stored within a storage unit 8 (to be described later) of the total control unit 5. The detection signal that has been input to the total control unit 5 is stored into the storage unit 8.

On the basis of predetermined settings (to be described later) stored within the storage unit 8 of the total control unit 5, the applied-voltage control unit 36 controls each voltage applied to the photomultiplier tubes 331 to 334 of the detectors 31 to 34.

Each photomultiplier tube 331 to 334 can vary detection sensitivity by changing the applied voltage. The detection sensitivity here is expressed in terms of a relationship between the amount of received light (the amount of light reaching the photomultiplier tubes 331 to 334) and the detection voltage value (the output voltages of the A/D converters 341 to 344). For example, given a constant amount of received light, increasing the applied voltages of the photomultiplier tubes 331 to 334 increases the detection voltage value (i.e., enhances the detection sensitivity). Conversely, reducing the applied voltage reduces the detection voltage value (i.e., lowers the detection sensitivity). In the photomultiplier tubes 331 to 334, when the applied voltage is changed under the amount of received light kept constant, if a ratio between the detection voltage values obtained before and after the applied voltage change (i.e., between the after-change detection voltage value and the before-change detection voltage value) is defined as R, and a value predetermined for the photomultiplier tube (i.e., a PMT multiplier) is defined as "k", the relationship between the applied voltage and the detection voltage value is represented by the following expression.

$$R=(\text{After-change applied voltage/Before-change applied voltage})^k \qquad \text{Expression 1}$$

The detection voltage value can be adjusted by changing the applied voltages of the photomultiplier tubes 331 to 334 in accordance with expression 1. The detection sensitivity can therefore be adjusted.

Under a command from the total control unit 5, the mechanism control unit 4 controls operation of driving units provided for the wafer mounting unit 1, a load port 41, a transport arm 42, and other sections.

The load port 41 is an interface unit for mounting thereon a vessel not shown, for example, FOUP (Front-Opening Unified Pod) as a wafer cassette, that accommodates the wafer 10 existing before or after being surface-inspected, and loading/unloading the mounted wafer 10 into/from the surface inspecting apparatus.

The transport arm 42 used to hold the wafer 10 and transport it to the surface inspecting apparatus carries the wafer 10 between the load port 41 and the wafer mounting unit 1.

Figure 2:
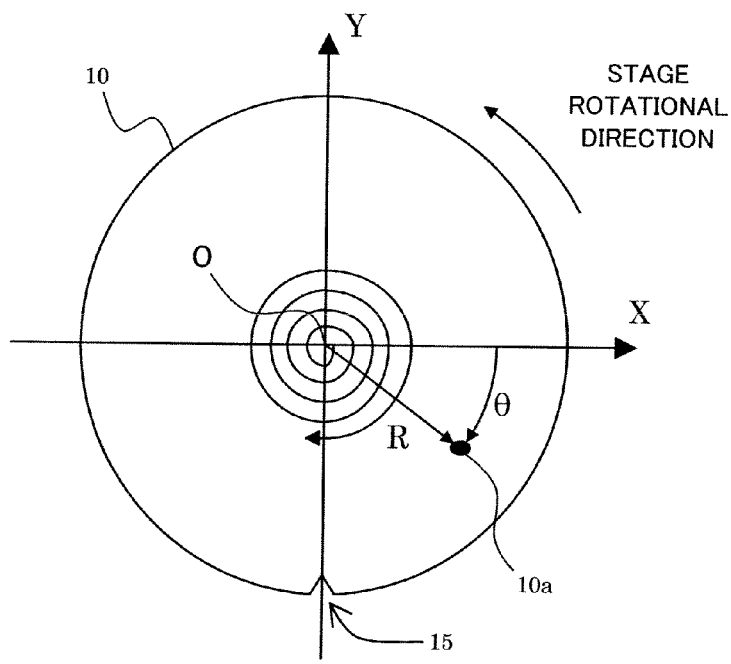
FIG. 2 shows a wafer in the embodiment of the present invention, and the way the wafer is scanned.

FIG. 2 shows the wafer 10 used in the present embodiment, and the way the wafer is scanned.

Referring to FIG. 2, the wafer 10 has a notch 15, at its circumferential edge, which serves as an orientation reference for the wafer 10.

If such a wafer 10 is disposed for its notch 15 to face downward, an X-Y coordinate system with an origin set up centrally on the wafer 10 can be defined. In addition, if a distance from the origin O of the X-Y coordinate system (i.e., the center of the wafer 10) is expressed as R, and an angle formed with respect to the X-axis by clockwise rotation of the wafer about the origin O of the X-Y coordinate system (i.e., a rotational angle) is expressed as θ, an R-θ coordinate system can be defined. Since the thus-defined X-Y coordinate system and R-θ coordinate system do not change in relationship, coordinate positions on both coordinate systems can be interchanged.

The illumination light is helically scanned over the surface of the wafer 10 (i.e., the surface to be inspected) by driving the wafer 10 rotationally as well as rectilinearly when the surface to be inspected is being irradiated with the illumination light. During scanning of the illumination light, position information on the rotary stage 12 and the rectilinear stage 13 (i.e., a direction of the rotary stage 12 and a position of the rectilinear stage 13 in a direction that the stage 13 can be moved) is output from the mechanism control unit 4 controlling the operation of the wafer mounting unit 1, to the total control unit 5. The position information is output as coordinate information on the irradiation position of the illumination light on the wafer 10.

The total control unit 5 that controls operation of the entire surface inspecting apparatus including the wafer mounting unit 1, the illumination optical system 2, the detection optical system 3, and the mechanism control unit 4, includes an input processing unit 6 and an information display unit 7 as well as the storage unit 8.

The input processing unit 6 is, for example, a keyboard, a mouse, a touchpanel, or the like, and enables entry of the various settings, commands, etc. that are used to inspect the surface of the wafer 10 and to calibrate the surface inspecting apparatus.

The information display unit 7 is, for example, a display unit that displays a screen for setting the data required for the surface inspection of the wafer 10 and for the calibration of the surface inspecting apparatus, results on the surface inspection and apparatus calibration (i.e., defect maps and histograms classified according to defect size), a slot number of the wafer, and other information. If the surface inspection and apparatus calibration results are determined to be abnormal, the information display unit 7 will also display a warning indicating that the abnormality has occurred.

The storage unit 8 is, for example, a hard disk, a memory, or the like, and holds position information on the rotary stage 12 and the rectilinear stage 13, and the detection signals from the detectors 31 to 34, associated with the position information. The storage unit 8 also holds the settings used for the surface inspection, and inspection recipes (to be described later), various parameters and software used for calibration of an automatic analyzer.

The total control unit 5 controls the constituent elements of the surface inspecting apparatus in accordance with the entered-data settings, software, and others stored within the storage unit 8.

(2) Correction of the Detection Sensitivity

Next, the calibration of the detection sensitivity in the surface inspecting apparatus of the present embodiment is described below.

The calibration of the detection sensitivity in the present embodiment is done by: first setting the surface inspecting apparatus in accordance with an inspection recipe (to be described later) that defines optical parameters and others; next irradiating with illumination light a contaminated standard wafer 110 (to be described later) that has a surface provided with a foreign object sample of a standard particle size, and detecting the light scattered from the foreign object sample; then calculating compensation parameters (to be described later) to calibrate the detection sensitivity of the photomultiplier tubes 331 to 334 so that relationships between the particle size of the foreign object sample and the detection voltage values of each photomultiplier tube 331 to 334 match a calibration curve; and finally, using the calculated compensation parameters to calibrate the detection sensitivity of the photomultiplier tubes 331 to 334.

In the present embodiment, compensation parameters relating to a plurality of optical conditions are calculated and managed, the optical conditions here referring to the illuminating conditions and detecting conditions each consisting of a combination of a plurality of illumination angles, illuminating and polarizing conditions, and light-receiving and polarizing conditions.

(2-1) Inspection Recipe

The inspection recipe is used to manage various conditions such as the optical conditions created through various processes, and inspection result display conditions, as one set of information. For example, the inspection recipe is provided for each kind of body to be inspected and each kind of information on the body to be inspected, and is stored within the storage unit 8.

(2-2) Contaminated Standard Wafer 110

Figure 3:
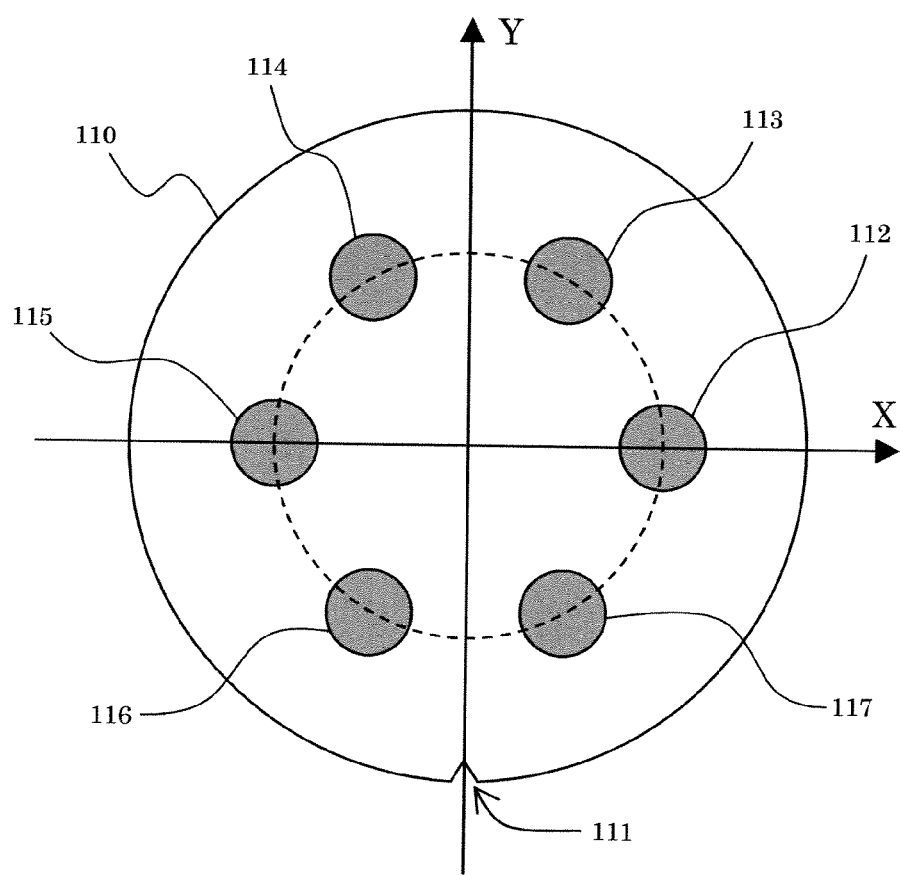
FIG. 3 shows a contaminated standard wafer in the embodiment of the present invention.

FIG. 3 shows the contaminated standard wafer 110 pertaining to the present embodiment.

Referring to FIG. 3, the contaminated standard wafer 110 has a notch 111 that serves as a reference for determining a direction of the contaminated standard wafer 110. An X-Y coordinate system with the contaminated standard wafer 110 as its center, and an R-θ coordinate system (not shown) are defined similarly to those of the wafer 10. A plurality of (say, six) PSL-coated areas, 112 to 117, each equally spaced in a circumferential direction and at an equal central distance from adjacent ones, are provided on the surface of the contaminated standard wafer 110. That is, the PSL-coated areas 112 to 117 are arranged at predefined coordinate positions on the contaminated standard wafer 110.

The PSL-coated areas 112 to 117 are areas coated with PSL (Poly Styrene Latex) particles. The PSL particles form a foreign object sample that has been controlled in particle size. Each PSL-coated area 112 to 117 is coated with PSL particles of a different size. The illumination light is scanned over the PSL-coated area coated with PSL particles of a size suitable for the calculation of the particular compensation parameters, and scattered light is detected using the photomultiplier tube 331 to 334.

The following describes how to calculate the detection voltage value for detecting the light scattered from the PSL-coated areas 112 to 117. First, a histogram of changes in detection voltage value and in detection rate is created for each PSL-coated area 112 to 117. The histogram exhibits a Gaussian distribution or a distribution approximate thereto. Its peak value is defined as the detection voltage value relating to the foreign object of the size of the PSL particles with which the PSL area to be inspected is coated.

While the present embodiment has used the contaminated standard wafer 110 having the plurality of PSL-coated areas, 112 to 117, that are each coated with PSL particles of a specific size, the present invention is not limited to this example and can use a plurality of contaminated standard wafers each coated with PSL particles of a specific size and may have detection voltage values calculated from each contaminated standard wafer.

(2-3) Compensation Parameter "Comp"

The compensation parameter is a compensation value for an initial value predefined as the applied voltages of the photomultiplier tubes 331 to 334 (i.e., a specified standard value or a data setting for first calibration). The compensation parameter is expressed as a ratio with respect to the initial value.

The detection sensitivity is adjusted by controlling the applied voltage of the photomultiplier tube 331 to 334 so that there is no difference between the calibration curve and the detection voltage value under the predefined optical conditions. The compensation parameter "Comp" used for the adjustment of the applied voltage is calculated using expression 1 shown above. In other words, the ratio between voltage value and detection voltage value, denoted by the calibration curve, is assigned to R in expression 1, then the after-change applied voltage is calculated, and a ratio between the initial value and the after-change applied voltage is calculated as the compensation parameter "Comp".

Here, if each optical condition is defined as "Cn" (C1 to Cn: n is a natural number), each photomultiplier tube is defined as "n" (1 to n: n is a natural number), a related compensation parameter is defined as "Comp (n, Cn)", and three element parameters, namely, a time-varying deterioration parameter "P", an optical characteristics parameter "Opt", and a sensor characteristics parameter "Lr", are defined according to influential factor, then the compensation parameter "Comp (n, Cn)" is represented by the following expression.

$$\mathrm{Comp}(n,\,Cn) = P(n) \times \mathrm{Opt}(n,\,Cn) \times Lr(n) \qquad \text{Expression 2}$$

(2-3.1) Time-varying Deterioration Parameter: P

The time-varying deterioration parameter is an element parameter relating to a time-varying deterioration state of the photomultiplier tube 331 to 334. The detection voltage of the photomultiplier tube 331 to 334 will decrease according to a total amount of light received from a start of operation. That is, the element parameter is an item for compensating for the deterioration of the photomultiplier tube, associated with light detection, and is common to all optical conditions. Irrespective of the kind of inspection recipe used for apparatus calibration, therefore, the detection sensitivity is adjusted using the time-varying deterioration parameter.

(2-3.2) Optical Characteristics Parameter: Opt

The optical characteristics parameter is an element parameter relating to variations in optical characteristics of each photomultiplier tube 331 to 334. This parameter is adjusted for each optical condition (each photomultiplier tube, illuminating and polarizing condition, detector changing condition, and so on). The element parameter is a parameter depending upon the optical condition, not adjustable by merely adjusting the detection sensitivity using the time-varying deterioration parameter.

(2-3.3) Sensor Characteristics Parameter: Lr

The sensor characteristics parameter is an element parameter relating to variations in respective sensor characteristics of each photomultiplier tube 331 to 334, that is, in linearity of an output signal concerning the amount of incident light. This element parameter is usually calculated during assembly of the apparatus or during calibration associated with replacement of the photomultiplier tube 331 to 334, and is stored within the storage unit 8. During periodical calibration, therefore, an independent element parameter is not calculated for each photomultiplier tube. The one stored within the storage unit 8 is used instead.

(2-4) Correction Sequence

Figure 4:
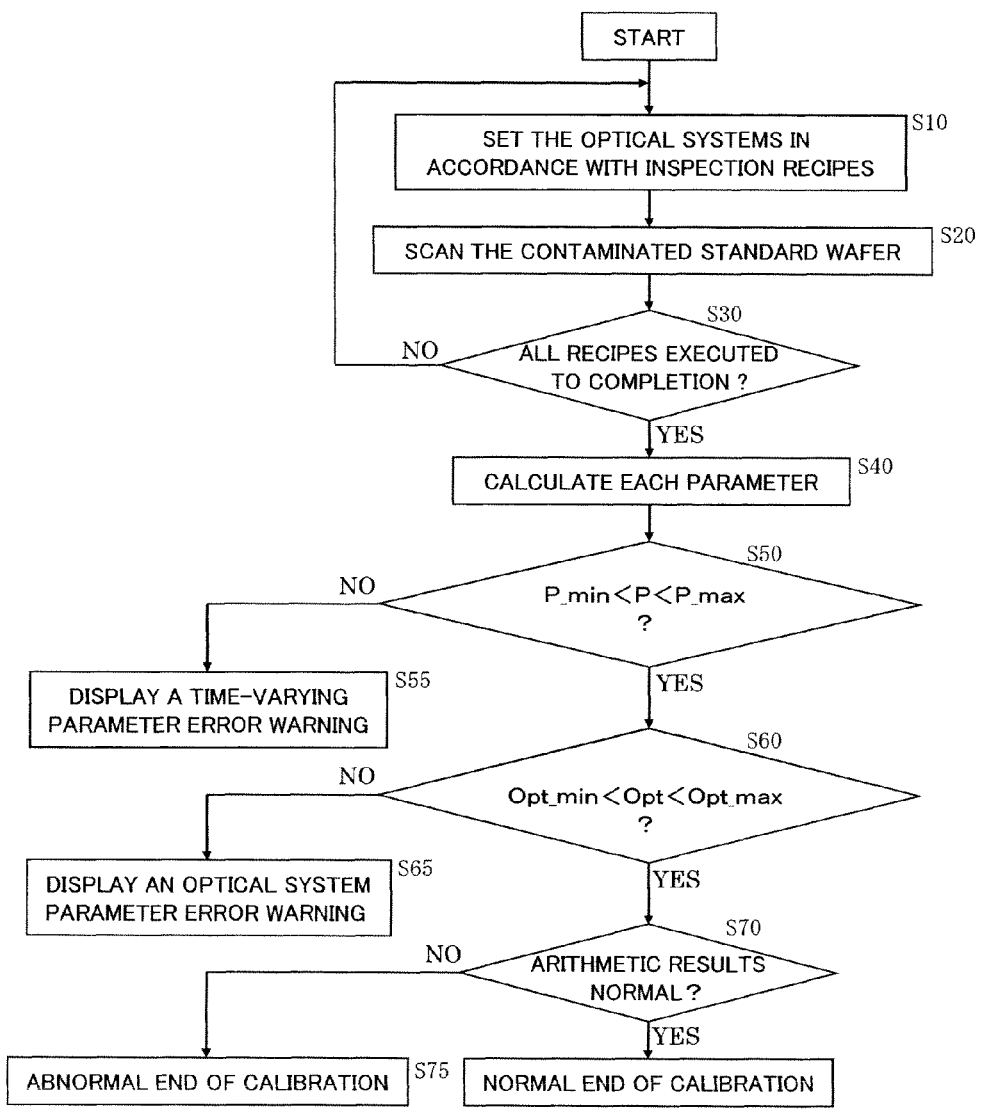
FIG. 4 is a flowchart showing a calibration process for surface inspection according to the embodiment of the present invention.

FIG. 4 is a flowchart showing the calibration process for the surface inspecting apparatus pertaining to the present embodiment.

First, one or more inspection recipes to be used for the calibration process are selected from all inspection recipes stored within the storage unit 8, and the calibration process is started.

The total control unit 5 first sets the optical systems of the surface inspecting apparatus in accordance with each selected inspection recipe (step S10). Next, the total control unit 5 scans illumination light over the surface of the contaminated standard wafer 110, associates scattered-light detection data (a detection voltage value) and detection coordinates, and stores the associated data and coordinates into the storage unit 8 (step S20).

The contaminated standard wafer 110 is scanned for all of the initially selected inspection recipes, and whether detection voltage values have been acquired is determined (step S30). If determination results are abnormal (NO), that is, if the inspection recipe is not yet executed, steps S10 and S20 will be repeated.

If the determination results in step S30 are normal (YES), the compensation parameter "Comp" and related time-varying deterioration parameter "P" and optical characteristics compensation parameter "Opt" will be calculated and temporarily stored as a useable compensation parameter and element parameters into the storage unit 8 (step S40).

Next, whether the time-varying deterioration parameter "P" stored as the useable compensation parameter in the storage unit 8 lies within a predefined normal data range (between a maximum allowable control value "P_max" and a minimum allowable control value "P_min"), and whether the optical system parameter "Opt" lies within a predefined normal data range (between a maximum allowable control value "Opt_max" and a minimum allowable control value "Opt_min") are determined (steps S50 and S60, respectively). If determination results in both steps are normal (YES), an operator will open a compensation parameter arithmetic result confirmation screen (see FIGS. 5 to 7 to be described later) and confirm measurement results (step S70). If operator confirmation results in step S70 are normal (OK), the configuration process will come to a normal end, or if the confirmation results are abnormal (NG), the configuration process will be aborted, indicating that the calibration is abnormal. Conversely, if the determination results in step S50 are abnormal (NG), abnormality of the time-varying deterioration parameter "P" will be displayed on the information display unit 7 and the calibration process will be terminated (step S55). If the determination results in step S60 are abnormal (NO), abnormality of the optical system parameter will be displayed on the information display unit 7 and the calibration process will be terminated (step S65).

(2-5) Compensation Parameter Arithmetic Results

The compensation parameter arithmetic results in the calibration process are displayed in the form of the compensation parameter arithmetic result confirmation screen on the information display unit 7 of the surface inspecting apparatus. During compensation parameter arithmetic result confirmation in the calibration process (step S70 of FIG. 4), the operator confirms arithmetic results referring to the compensation parameter arithmetic result confirmation screen. The compensation parameter arithmetic result confirmation screen includes the following three confirmation screens.

(2-5.1) Compensation Parameter Arithmetic Result confirmation screen 171 (Main screen)

FIG. 5 shows the screen for confirming compensation parameter arithmetic results in the calibration process.

The compensation parameter arithmetic result confirmation screen 171 in FIG. 5 includes: an inspection recipe display area 172 for displaying a list of inspection recipes; a result display area 173 for displaying arithmetic results on the compensation parameter; buttons 174 and 175 for displaying a summary confirmation screen 271 and a history confirmation screen 371, respectively, the screens 271 and 371 being described later herein; an UPDATE button 176 for incorporating computed useable compensation parameters as compensation data for the surface inspecting apparatus; and a CANCEL button 177 for terminating the calibration process without incorporating the compensation data.

Selection of an inspection recipe 178, for example, in the inspection recipe display area 172 displays a name of the inspection recipe and an inspection execution date/time in display areas 179 and 180, respectively. The selection additionally displays compensation parameter arithmetic results on the inspection recipe 178, in the result display area 173. The present example is described assuming that the inspection employs a recipe intended to calculate the compensation parameter relating to time-varying deterioration, that is, an inspection recipe for calculating a compensation parameter independent of the optical characteristics parameter and applied to a case in which the sensor characteristics parameter is fixed.

The result display area 173 shows a dimension of each detector in the surface inspecting apparatus (10 detectors are shown by way of example in FIG. 5), a reference detection value, a detection value in the calibration process, compensation parameter update data (update candidates), and previous values of each compensation parameter.

The dimension of each detector is a photomultiplier tube diameter of the detector, and the example of FIG. 5 denotes that detectors L1 to L6 each use an independent photomultiplier tube of a 50-nm diameter and that detectors H1 to H4 each use an independent photomultiplier tube of a 60-nm diameter.

The reference value is expressed in terms of a detection voltage value provided for as a reference value (e.g., a specified value) in the selected inspection recipe, and upper and lower allowable discrepancies (margins) of the detection voltage value.

The detection value is expressed in terms of the detection voltage value in the calibration process and a difference between the detection voltage value and the reference value. That is, the values shown in an area 181 denoted by a dotted line are the detection voltage values of each photomultiplier tube under conditions of the inspection recipe 178. The above difference is displayed in color-coded form according to a particular rate of the difference to the reference value. For example, if the difference, as with that relating to the detectors L1, L3, lies within the margin range and a predetermined margin rate is exceeded (e.g., if the difference is 15 or more), areas 183 and 184 denoted by a dotted line will be displayed in a color indicative of caution, such as yellow. If the difference, as with that relating to the detector L4, exceeds the margins, an area 185 denoted by a solid line will be displayed in a color indicative of a warning, such as red. The method of displaying cautionary or warning information is not limited to the above and it suffices just to caution or warn the operator, as by inverse display or blinking display. The display area of the detection value may present the detection value in terms of, for example, the detection voltage value in the calibration process and a difference between the detection voltage value and the reference value, and margins may be set for the ratio.

Compensation parameter candidates that have been calculated in the calibration process are displayed as update data. When the UPDATE button 176 on the screen is pressed, values displayed in an area 182 denoted by a dotted line will be incorporated as compensation values. FIG. 5 shows an example of time-varying element parameter update data.

The previous values denote the compensation parameters obtained as previous calibration results (after incorporation of previous update data). The compensation parameters here refer to the time-varying deterioration parameter, the optical characteristics parameter, and the sensor characteristics parameter.

A press (selection) of the button 174 on the compensation parameter arithmetic result confirmation screen 171 changes the screen to the summary confirmation screen 271 (see FIG. 6 that follows). A press (selection) of the button 175 on the compensation parameter arithmetic result confirmation screen 171 changes the screen to the history confirmation screen 371 (see FIG. 7 that follows).

(2-5.2) Summary Confirmation Screen 271

FIG. 6 shows the summary confirmation screen 271 in the calibration process.

The summary confirmation screen 271 in FIG. 6 has a difference listing area 272 that displays a list of differences between the detection voltage values and reference values in each inspection recipe, and a button 273 that returns screen control to the compensation parameter arithmetic result confirmation screen 171.

In the listing area 272, the difference between the detection voltage value and reference value of each detector in the surface inspecting apparatus is displayed for each set of optical conditions (each inspection recipe), and data concerning eight detectors is shown by way of example in FIG. 6. The set of optical conditions includes, in addition to the inspection recipe number (condition set identification number), the illumination angle, polarizing conditions, and more in each inspection recipe. Difference display areas are each displayed in color-coded form according to the particular rate of the difference to the reference value. For example, if the difference, as with that relating to the detectors L1, L3, H1, lies within the margin range and a predetermined margin rate is exceeded (e.g., if the difference is 15 or more), areas 275 to 278, 280 denoted by a dotted line will be displayed in a color indicative of caution, such as yellow. If the difference, as with that relating to the detector L4, exceeds the margins, then an area 274 denoted by a dotted line, and an area 279 denoted by a solid line will be displayed in a color indicative of a warning, such as red.

In the listing area 272, if, as with that relating to the detector L4, the difference of the detection value with respect to the reference value is in excess of the margins independently of the optical conditions (inspection recipe), for example, this indicates that the photomultiplier tube of the detector L4 has deteriorated and requires replacement. If the difference of the detection value with respect to the reference value is in excess of the margins independently of the detectors under specific optical conditions such as the optical condition set 5, this indicates that sensitivity is changing under the optical conditions.

The listing area 272 may show the ratio between the detection voltage value and the reference value.

(2-5.3) History Confirmation Screen 371

Figure 7:
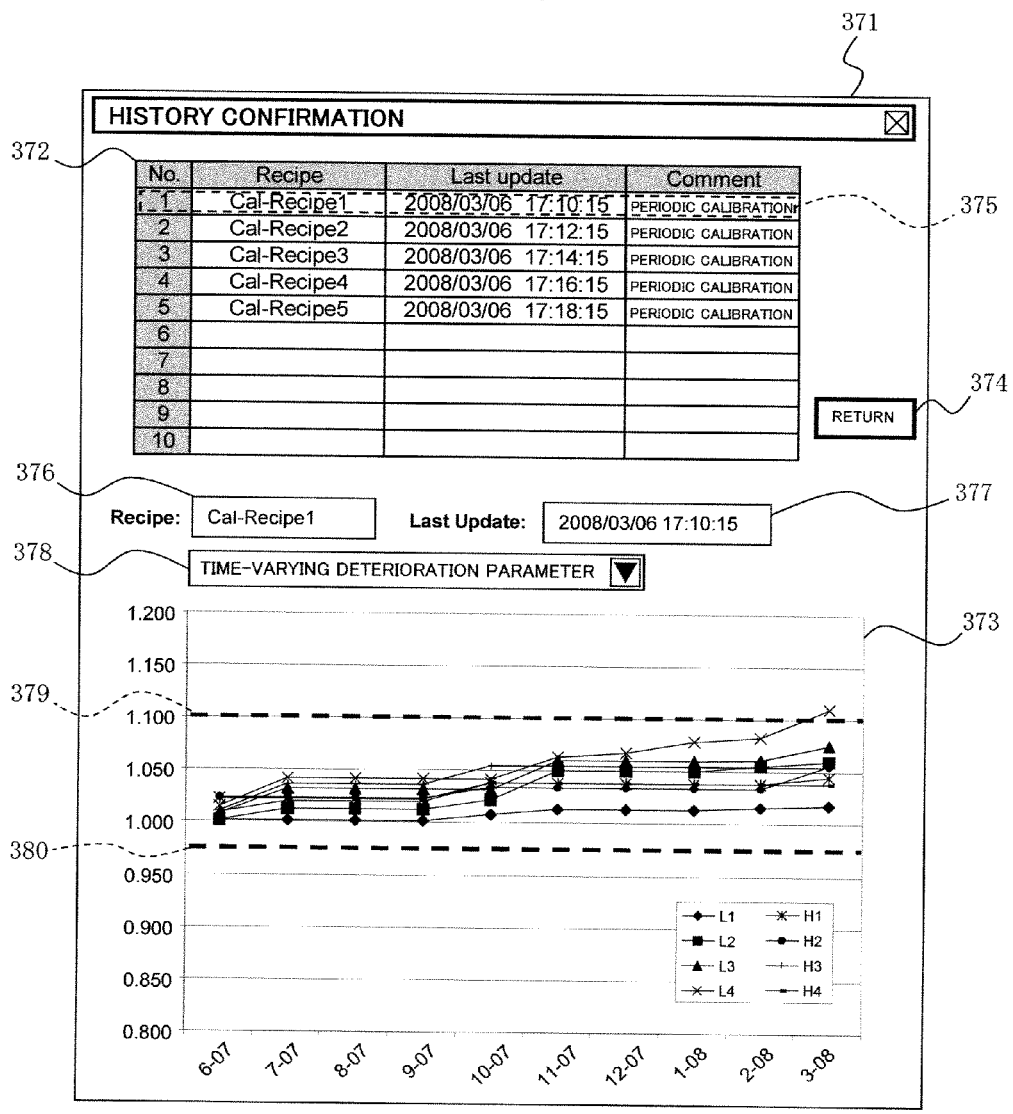
FIG. 7 shows a screen for confirming history in the calibration process for the surface inspecting apparatus according to the embodiment of the present invention.

FIG. 7 shows the history confirmation screen 371 in the calibration process.

The history confirmation screen 371 in FIG. 7 has an inspection recipe listing area 372 that displays a list of inspection recipes, a graph display area 373 that shows an element parameter for compensation chronologically, and a button 374 that returns screen control to the compensation parameter arithmetic result confirmation screen 171.

For example, if an inspection recipe 375 is selected in the inspection recipe listing area 372, a name of the inspection recipe, an execution time of the inspection, and a name of the element parameter will be displayed in display areas 376 to 378, respectively, and the compensation element parameter arithmetic results relating to the inspection recipe 375 will be displayed in the graph display area 373. Display of the time-varying deterioration parameter "P" is described here by way of example.

Chronological changes in the time-varying deterioration parameter of each detector (in FIG. 7, eight detectors) in the surface inspecting apparatus are displayed in graphical form for past multiple (e.g., 10) repetition cycles of the calibration process. In addition, the maximum allowable control value "P_max" and minimum allowable control value "P_min" of the time-varying deterioration parameter are shown as dotted lines 379 and 380, respectively. The time-varying deterioration parameter "P" is set to be 1.0, for example, for initial adjustment, and this value is updated with each repetition cycle of the calibration process.

It can be seen that in the graph display area 373, while a left half of the time-varying deterioration parameter of each detector exhibits values close to the initial value of 1.0, these values later increase with time, that is, with an increasing total amount of light reaching the photomultiplier tube of the detector. It can be seen that for example, if, as with that relating to the detector L4, the time-varying deterioration parameter is in excess of its maximum allowable value, the photomultiplier tube of the detector L4 has deteriorated and requires replacement.

During chronological display of the changes in the optical characteristics parameter, if the optical system is normal, the changes will be gentle within a definite range, but if the optical system becomes abnormal, the changes will overstep the definite range, so that occurrence and timing of the abnormality can be confirmed.

(3) Effects of the Present Embodiment

In the present embodiment employing the above-described configuration, each compensation parameter for the compensation of the voltage applied to the photomultiplier tubes in the detectors is managed in the form of being separated into the element parameters corresponding to the plurality of factors influencing the detection sensitivity. This enables the operator to verify adequacy of the detection sensitivity adjustment while synthetically considering various parameters such as the deterioration states and temperature drifts of the elements constituting the surface inspecting apparatus. The detection sensitivity in the surface inspecting apparatus can therefore be easily calibrated.

This, in turn, enables even an operator low in skill level of calibration to perform the calibration as easily as a highly skilled operator can. The skill level required for the operator who performs the calibration, therefore, is suppressed and efficiency of the calibration and that of the entire surface inspection including the calibration are improved.

(4) Miscellaneous

While the embodiment of the present invention has been described above, the embodiment can be changed and modified in various forms within the spirit and ambit of the invention.

The apparatus of the present embodiment is configured to calculate the compensation parameter "Comp" using the contaminated standard wafer 110 whose surface is provided with a foreign object sample of a standard particle size. However, the apparatus is not limited to this calculating method. The apparatus may use a standard light source that generates light of predetermined luminance, and detect with the detectors 31 to 34 the light emitted from the standard light source to calculate the compensation parameter "Comp" for compensating the detection sensitivity of each photomultiplier tube 331 to 334 so that a relationship between the luminance of the light from the standard light source and a detection voltage value of the photomultiplier tube 331 to 334 matches a calibration curve.

In addition, while the surface (surface to be inspected) of the wafer 10 is being irradiated with illumination light, the wafer 10 is driven rotationally by the rotary stage 12 in addition to being driven rectilinearly by the rectilinear stage 13, and the illumination light is scanned over the surface of the wafer 10 in helical fashion for calibration. The scan, however, may be in X-axial and Y-axial directions.

Furthermore, the illumination light emitted to the wafer 10 by the irradiation optical system 2 may have a linear shape on the wafer surface.

Besides, the detection optical system 3 may be an imaging system that uses mirrors, lenses, and the like, or may include a spatial filter that removes specific beams of diffracted light in scattered light, or may be constructed to condense scattered light using an oval sphere.

Moreover, while each detector is constructed to detect scattered light using a photomultiplier tube, the detector may be constructed to detect scattered light using a time-delayed integration-type sensor or a CCD sensor.

DESCRIPTION OF THE REFERENCE NUMERALS

1 Wafer mounting unit
2 Illumination optical system

3 Detection optical system
4 Mechanism control unit
5 Total control unit
6 Input processing unit
7 Information display unit
8 Storage unit
10 Wafer
11 Wafer chuck
12 Rotary stage
13 Rectilinear stage
14 Base
15 Notch
20 Laser light source
21 Illumination light polarizing filter
22, 23 Reflecting mirrors
24 Illumination angle switching mirror
31 to 34 Detectors
41 Load port
42 Transport arm
110 Contaminated standard wafer
111 Notch
113 to 117 PSL-coated areas
311 to 314 Condensing lenses
321 to 324 Detected-light polarizing filters
331 to 334 Photomultiplier tubes

The invention claimed is:

1. A surface inspecting apparatus comprising:
a light unit that irradiates with illumination light a surface of a body to be inspected;
a scanner that scans the light irradiated from the light unit over the surface of the to-be-inspected body;
at least one light detector that detects the light scattered from the surface of the body to be inspected;
a processor configured to:
use a predefined reference value, as well as a detection result on measuring light incident upon the light detector from a measuring-light generator that generates the measuring light that serves as a reference for measuring detection sensitivity of the light detector, to compute a sensitivity correction value for correcting the detection sensitivity of the light detector;
separate the sensitivity correction value into element parameters corresponding to a plurality of factors influential upon detection sensitivity of the surface inspecting apparatus; and
memory, associated with the processor, for storing the element parameters obtained from the separation by the processor.

2. The surface inspecting apparatus according to claim 1, wherein:
the measuring-light generator includes a reference body to be inspected, the reference body being formed to generate measuring light that serves as a reference for the illumination light from the light unit.

3. The surface inspecting apparatus according to claim 1, wherein:
the measuring-light generator includes a light source that emits measuring light serving as a reference into the light detector.

4. The surface inspecting apparatus according to claim 1, wherein:
the plurality of element parameters include an element parameter relating to a time-varying deterioration state of the light detector.

5. The surface inspecting apparatus according to claim 1, wherein:
the plurality of element parameters include an element parameter relating to optical characteristics of the light detector.

6. The surface inspecting apparatus according to claim 1, wherein:
the plurality of element parameters include an element parameter relating to linearity characteristics of the light detector.

7. The surface inspecting apparatus according to claim 1, further comprising:
a display that displays the element parameters in a chronological fashion.

8. The surface inspecting apparatus according to claim 1, further comprising:
a display that displays either a difference of the detection result with respect to a reference value, or a ratio of the detection result to the reference value.

9. The surface inspecting apparatus according to claim 1, further comprising:
a display that display a warning for an operator if at least one of the element parameters oversteps a predefined range.

10. The surface inspecting apparatus according to claim 1, wherein:
if at least one of the element parameters oversteps a predefined range, the processor determines whether the overstepping state has been caused by time-varying deterioration or optical conditions.

11. A method for calibrating a surface inspecting apparatus that includes a light unit that irradiates with illumination light a surface of a body to be inspected, a scanner that scans the light irradiated from the light unit over the surface of the to-be-inspected body, and at least one detector that detects the light scattered from the surface of the body to be inspected, the method comprising the steps of:
using a predefined reference value, as well as a detection result on measuring light incident upon the light detector from a measuring-light generator that generates the measuring light that serves as a reference for measuring detection sensitivity of the light detector;
computing, by a processor, a sensitivity correction value for correcting the detection sensitivity of the light detector;
separating, by the processor, the sensitivity correction value into element parameters corresponding to a plurality of factors influential upon detection sensitivity of the surface inspecting apparatus; and
storing, in memory associated with the processor, the element parameters obtained from the separation.

* * * * *